United States Patent
Huet et al.

(10) Patent No.: US 8,622,959 B2
(45) Date of Patent: Jan. 7, 2014

(54) SYSTEM FOR INJECTING A LIQUID INTO A BODY, SUCH AS THAT OF A PATIENT

(75) Inventors: Gildas Huet, Chantilly (FR); Eric Perouse, Paris (FR); Thomas Walter, Rueil-Malmaison (FR)

(73) Assignee: Laboratoires Perouse, Ivry le Temple (FR)

( * ) Notice: Subject to any disclaimer, the term of this patent is extended or adjusted under 35 U.S.C. 154(b) by 159 days.

(21) Appl. No.: 13/055,338

(22) PCT Filed: Jul. 22, 2009

(86) PCT No.: PCT/FR2009/051467
§ 371 (c)(1),
(2), (4) Date: Mar. 10, 2011

(87) PCT Pub. No.: WO2010/010296
PCT Pub. Date: Jan. 28, 2010

(65) Prior Publication Data
US 2011/0178478 A1    Jul. 21, 2011

(30) Foreign Application Priority Data
Jul. 23, 2008  (FR) .................................... 08 55032

(51) Int. Cl.
*A61M 5/00* (2006.01)
*A61M 5/32* (2006.01)
(52) U.S. Cl.
USPC ............................. 604/110; 604/162; 604/263

(58) Field of Classification Search
USPC .............. 604/93.01, 110, 131, 163, 171, 181, 604/187, 263, 192–198, 164.01–170.09
See application file for complete search history.

(56) References Cited

U.S. PATENT DOCUMENTS

| 4,573,994 A | 3/1986 | Fischell et al. |
| 4,846,807 A | 7/1989 | Safadago |

FOREIGN PATENT DOCUMENTS

| FR | 2 886 857 A | 12/2006 | |
| FR | 2886857 | * 12/2006 | ............... 604/288.04 |
| WO | 98/52638 A | 11/1998 | |

* cited by examiner

*Primary Examiner* — Nicholas Lucchesi
*Assistant Examiner* — Rebecca E Eisenberg
(74) *Attorney, Agent, or Firm* — Sughrue Mion, PLLC (57) ABSTRACT

The invention relates to a system for injecting a liquid into a body, comprising an implantable chamber disposed under the skin and an injection device including: a base bearing an injection needle having a free end that is intended to be inserted into the chamber; an injection conduit connected to the needle; means for extracting the needle; means that can be actuated to generate excess pressure in the injection conduit; synchronization means between the extraction means and the generation means for actuating the generation means during a needle extraction phase. The synchronization means can essentially only actuate the generation means when the free end of the needle is located in the chamber during the needle extraction phase.

11 Claims, 5 Drawing Sheets

SYSTEM FOR INJECTING A LIQUID INTO A BODY, SUCH AS THAT OF A PATIENT

The present invention relates to a system for injecting liquid into a body, such as that of a patient, of the type that comprises:
an implantable chamber capable of being disposed under the patient's skin and extended by a catheter capable of traveling in a blood vessel to an organ, where the liquid must be injected, and
an injection device including:
a base bearing an injection needle, the needle having a pointed free end, intended to be inserted into the body and engaged in the implantable chamber,
an injection conduit connected to the needle,
means for extracting the needle from the patient, including a push element mounted such that it can slide in relation to the base between a needle use position and a needle extraction position;
activatable means for generating excess pressure in the injection conduit, normally inactive,
synchronizing means for synchronization between the extraction means and the generating means to activate the generating means during an extraction phase of the needle.

In certain pathologies, it is necessary to inject a daily dose of liquid medication directly into a patient's organ. To that end, it is known to use an injection system including a chamber permanently implanted on the patient's chest and disposed under the skin. This chamber is extended by a catheter traveling in a blood vessel to the organ, where the drug dose must be distributed. The implantable chamber includes a reservoir having a septum that can be perforated along the contact surface of the skin.

To inject the drug dose, the needle of the system is engaged through the patient's skin in the implantable chamber and the drug dose is injected into said chamber through the needle.

The injection system includes a holder integral with the needle. The holder is extended by a tube whereof one end is connected to the injection needle, and the other end of which is equipped with a connector making it possible to connect a syringe or a reservoir of a drug dose to be injected.

To remove the needle from the implantable chamber, the practitioner grasps the holder of the device and pulls the needle out of the patient.

The force deployed by the practitioner to remove the needle is relatively significant, such that the risk of pricking by rebound phenomenon is high when the needle leaves the skin. To avoid that risk, the injection device is commonly provided with an extraction assembly comprising a needle protection structure that receives the needle when it is removed to secure the needle and prevent the practitioner from being pricked.

When the needle is removed, it adheres to the septum, which rises, the inner volume of the chamber increases, thereby creating strong suction. This suction is at the catheter end that is generally located in a blood vessel. Blood then comes into the lumen of the catheter. Then, as the needle comes further out of the septum, the adhesion effect decreases, the septum then resumes its initial shape and the inner volume of the chamber decreases without reaching its initial value. A residual volume of blood then remains at the end of the catheter.

This residual volume of blood causes a deposition of fibrin (or other materials) that causes, over time, a decrease in the flow rate of the implantable chambers that can go as far as obstruction. The chamber must therefore be replaced frequently.

This problem was, for example described in the article "Variations de pression induites par le retrait de l'aiguille sur une Chambre à catheter implantable" ["Pressure variations caused by the removal of needles from implantable catheter chambers"] by S. Millet, L. Mercier, L. Ronchi, published in the Annales Françaises d'Anesthésie et de Réanimation, volume 24 2005, page 1117.

To offset this problem, FR 2 886 857 A1 teaches a system of the aforementioned type, in which the means for generating an over-pressure are provided in the extraction assembly to generate an over-pressure in the injection conduit during the extraction.

However, with such a system, the generation of the over-pressure in the injection conduit is not optimized during removal of the needle. The means for generating the over-pressure is in fact too significant in light of the volume of blood able to penetrate the catheter during removal of the needle.

The invention therefore aims to improve the generation of the over-pressure generated during a suitable phase of the removal of the needle, in order to avoid an obstruction of the catheter by greatly reducing, or even eliminating the residual volume of blood at the catheter end.

To that end, the invention relates to an injection system of the aforementioned type, characterized in that the synchronization means can actuate the generating means substantially only when the free end of the needle is located in the implantable chamber, during the needle extraction phase.

According to other embodiments, the injection system comprises one or several of the following features, considered alone or according to all technically possible combinations:
the synchronization means is capable of actuating the generating means substantially during the entire duration of the needle extraction phase, during which the free end of the needle is situated in the implantable chamber;
said generating means comprises a flexible segment formed in the injection conduit, a cam surface integral with the push element, and a bearing surface integral with the base, to compress said flexible segment between the cam surface and the bearing surface, during sliding of the push element towards the extraction position of the needle;
the cam surface is formed by two distinct and adjacent faces of the push element, the first face being inclined relative to the direction of movement of the push element and oriented towards the bearing surface, and the second face being substantially parallel to the direction of movement of the push element;
the length of the orthogonal projection of the first face over the direction of movement of the push element is substantially less than or equal to the height of the implantable chamber in the direction of movement of the push element;
the length of the second face in the direction of movement of the push element is greater than or equal to the sum of 3 mm and a securing distance between the free end of the needle in the extraction position and the lower end of the push element, the sliding of the push element towards the extraction position of the needle taking place from top to bottom;
the incline angle between the first face and the direction of movement of the push element is between 10° and 35°, preferably equal to 14°;

the cam surface can be moved substantially perpendicular to the flexible segment during extraction of the needle;

the injection device comprises additional means for covering the injection conduit, arranged upstream of the means for generating the over-pressure;

the base includes a needle holder and a sleeve, said sleeve being hinged relative to the needle holder and defining a sliding passage of the push element.

The invention and its advantages will be better understood upon reading the following description, provided solely as an example, done in reference to the appended drawings, in which.

Figure 1:
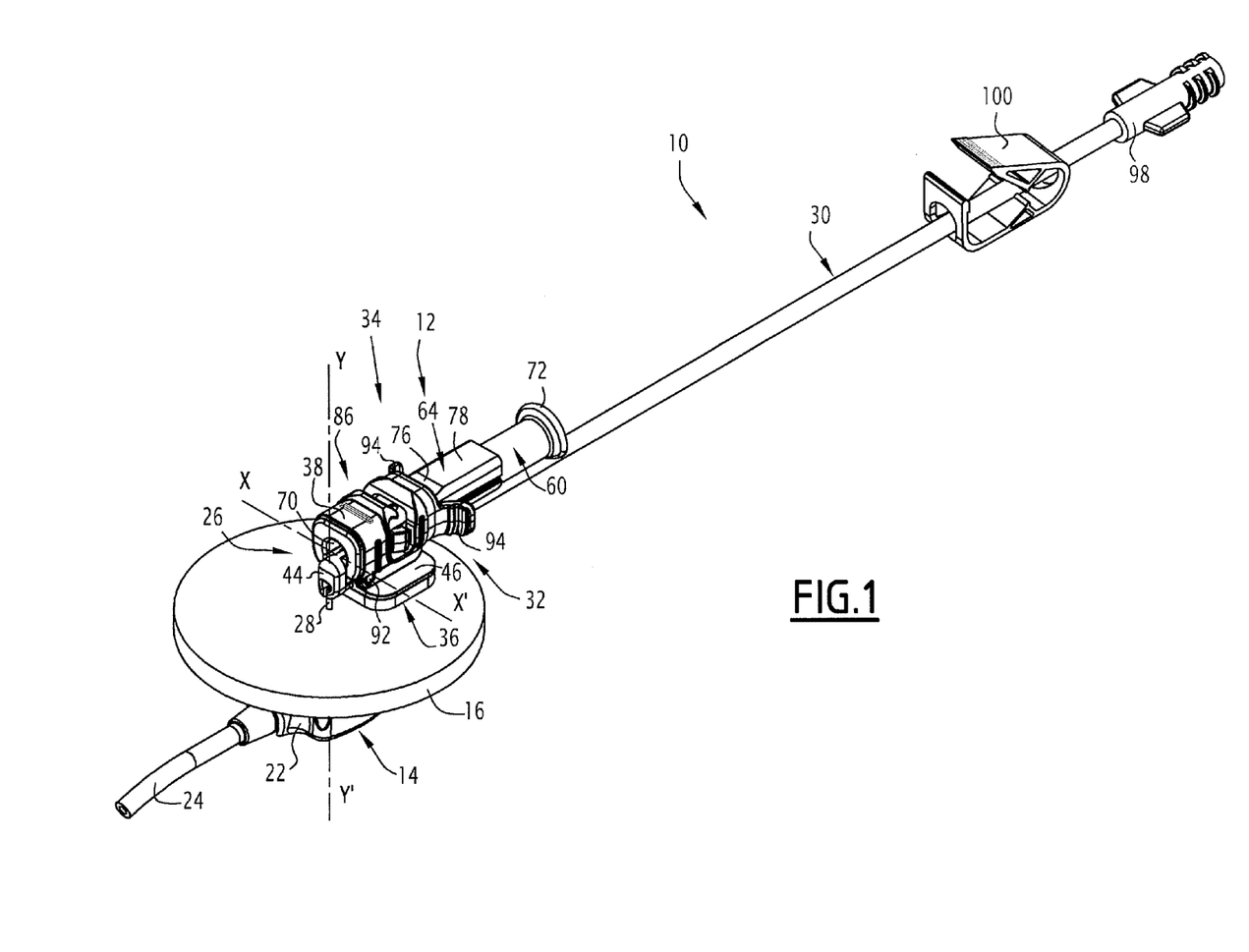
FIG. 1 is a perspective view of an injection system in the in use configuration according to the invention, a needle of the system being engaged through the skin of a patient in a chamber.

In FIG. 1, an injection system 10 includes an injection device 12 and an implantable chamber 14 disposed under a patient's skin 16.

Figure 3:
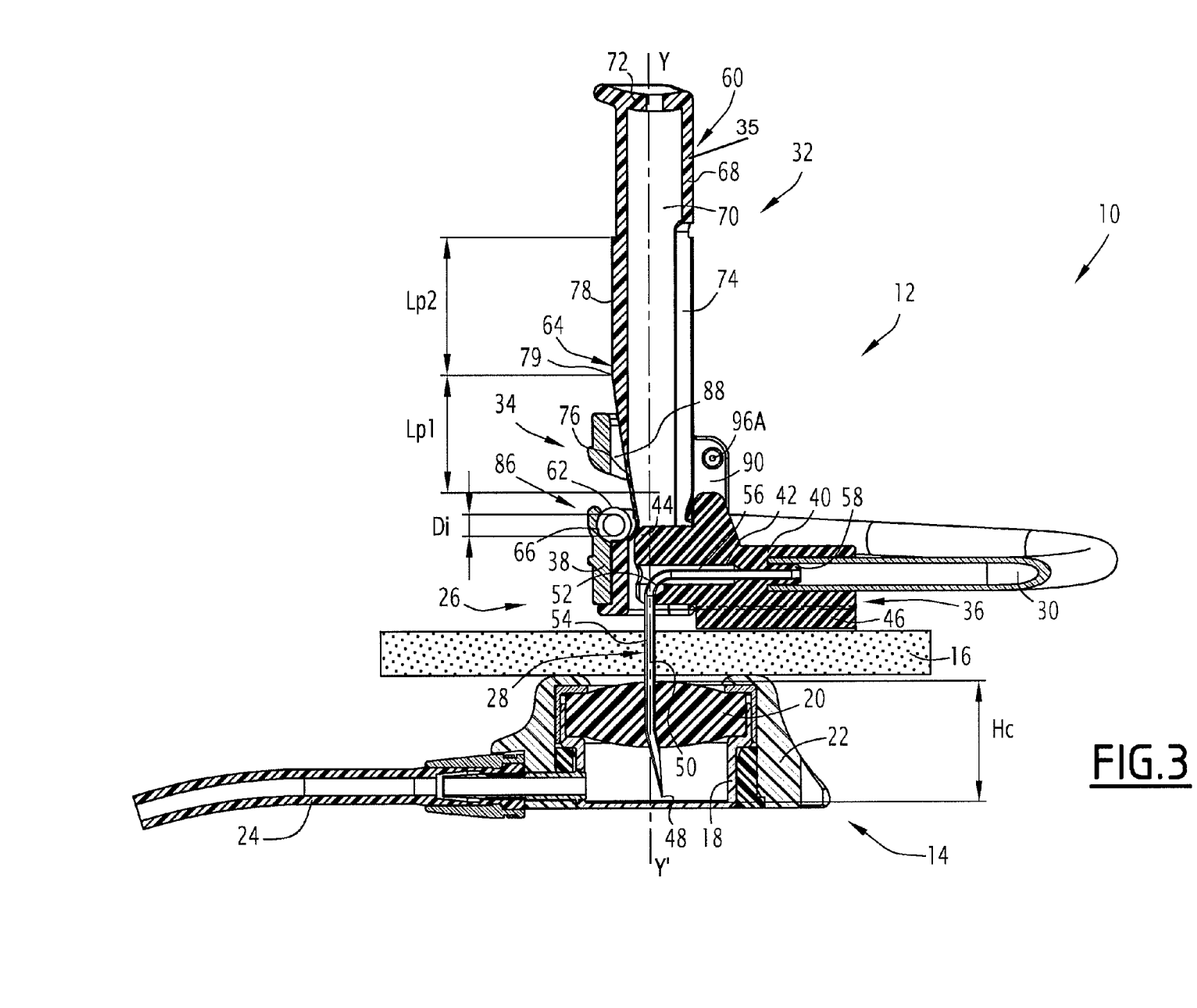
FIG. 3 is a cross-sectional view along plane III of FIG. 2.

The chamber 14 has a substantially cylindrical reservoir 18 defined, on its upper face, in contact with the inner surface of the skin 16, by a perforable membrane 20, visible in FIG. 3 and also called a septum. The septum 20 is elastically deformable and sealed. It is for example made from silicone. The reservoir 18 is laterally surrounded by a protective housing 22 and connected to a catheter 24 for conveying a drug solution towards an organ, not shown. The catheter 24 travels in a blood vessel, not shown, to the organ.

Figure 2:
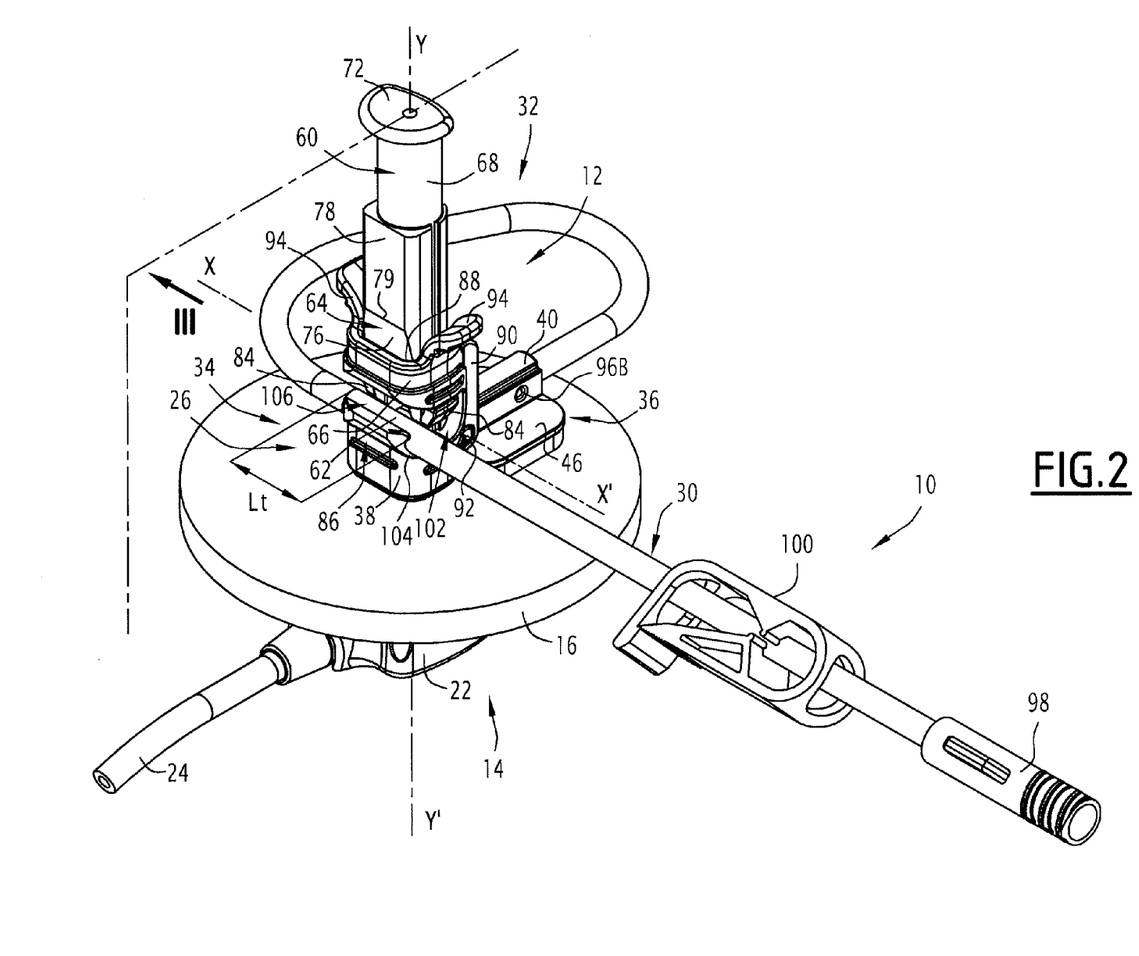
FIG. 2 is a perspective view of the injection system in the extraction configuration according to the invention, the needle being ready to be removed from the implantable chamber.

In FIGS. 1 and 2 the injection device 12 comprises a base 26 supporting an injection needle 28, and an injection conduit 30 connected to the needle 28. The injection device 12 also includes extraction means 32 for removing the needle from the patient, an activatable means 34 for generating an over-pressure in the injection conduit 30, normally inactive, and a synchronization means 35 between the extraction means 32 and the generating means 34 to activate the generating means 34 during an extraction phase of the needle 28.

The base 26 includes a needle holder 36 and a sleeve 38 hinged relative to the needle holder 36.

The holder 36 includes an elongated central core 40, visible in FIG. 2 and generally cylindrical, passed all the way through by an axial lumen 42, visible in FIG. 3, for conveying liquid to the needle 28. The needle 28 is secured to one end, called downstream following the direction of travel of the liquid, of the core 40, which forms a head 44. On the side of the holder oriented towards the needle 28, the holder 36 includes a bearing plate 46 extending along the length of the holder, with the exception of the end region forming the head 44, which protrudes relative to the bearing plate 46.

The needle 28, visible in FIG. 3, has a pointed curved free end 48 intended to be inserted in the patient and engaged in the chamber 14. The free end 48 emerges laterally relative to the general axis of the needle 28. The needle 28 inwardly defines a passage 50 for injecting liquid.

The needle 28 forms, for example, a bend 52 extended on the pointed side 48 by a main segment 54 having vertical axis Y-Y' and, on the side opposite the point 48, with a perpendicular connecting segment 56 engaged in the axial lumen 42 from the head 44. Near the upstream end of the core 40, the lumen 42 is extended in a stud 58 ensuring the connection of the conduit 30.

Figure 5:
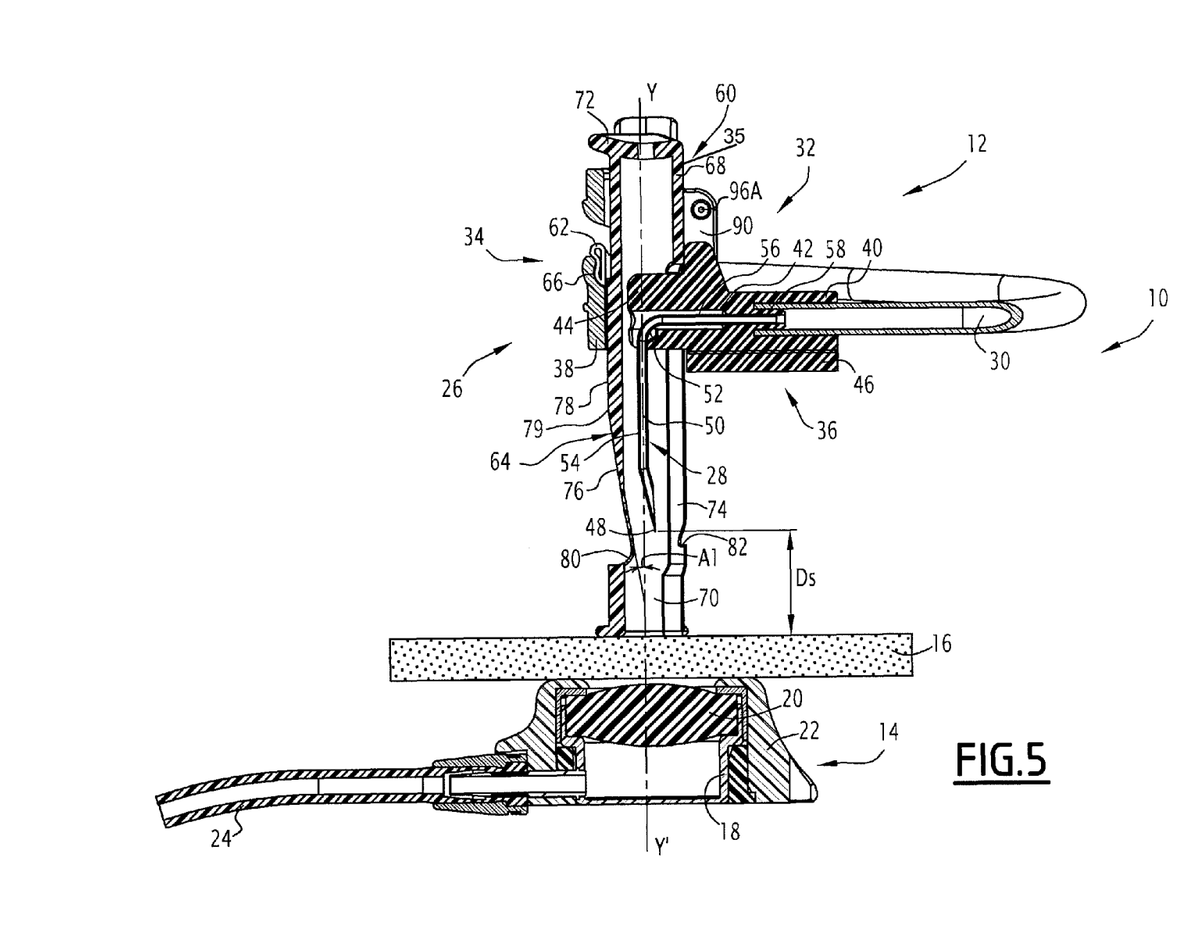
FIG. 5 is a view similar to that of FIG. 3, the needle being completely removed from the implantable chamber.

The means 32 for extracting the needle from the patient comprises the base 26 and a push element 60 slidingly mounted relative to the base 26. The push element 60 can be moved between a use position of the needle 28 or an inactive position of the extraction means 32 as illustrated by FIGS. 1 to 3, and an extraction position of the needle 28 as illustrated by FIG. 5.

The means 34 for generating an over-pressure in the injection conduit 30 during the extraction of the needle 28, comprises a flexible segment 62 formed in the injection conduit 30, a cam surface 64 integral with the push element 60 and a bearing surface 66 integral with the base 26, to compress said flexible segment 62 between the cam surface 64 and the bearing surface 66, during sliding of the push element 60 towards the extraction position of the needle 28.

In the described embodiment, the compression of the flexible segment 62 is radial and perpendicular to the needle 28. The cam surface 64 can be moved substantially perpendicular to the flexible segment 62 during the extraction of the needle 28.

The length Lt, visible in FIG. 2, of the flexible segment 62 intended to be compressed between the cam surface 64 and the bearing surface 66 is between 5 and 15 mm, preferably equal to 10 mm. The inner diameter Di of the uncompressed flexible segment 62 is between 1 and 3 mm, preferably equal to 2 mm.

The push element 60 is formed by a rod 68 generally hollowed out and open at one end, called lower end, facing the needle 28, the sliding of the push element 60 towards the extraction position of the needle 28 being done from top to bottom. The rod 68 defines a cylindrical inner volume 70 for receiving the needle 28, covered at its upper end by a bearing-finger 72, as shown in FIG. 3. The rod 68 forms a cap protecting the needle 28, in the extraction position of the needle 28, as shown in FIG. 5. The rod 68 is open, from its front end, by a slot 74 extending along the length of the push element over the main portion of the length thereof. The width of the slot 74 is sufficient to receive the central core 40.

The cam surface 64 is formed by two distinct and adjacent faces 76, 78 of the push element 60. The two faces 76, 78 are connected to each other by a shared edge 79. The first face 76 is inclined relative to the direction of movement of the push element 60 and oriented towards the bearing surface 66. The second face 78 is substantially parallel to the direction of movement of the push element 60. The cam surface 64 has, in longitudinal cross-section, a convex profile oriented towards the bearing surface 66.

The length Lp1 of the orthogonal projection of the first face 76 over the direction Y-Y' of movement of the push element is substantially smaller than or equal to the height Hc of the chamber 14 along the direction Y-Y' of movement of the push element, as shown in FIG. 3. The height Hc is equal to the sum of the depth of the reservoir 18 and the thickness of the septum 20.

The length Lp2 of the second face 78 in the direction Y-Y' of movement of the push element is greater than or equal to the sum of 3 mm and a securing distance Ds, visible in FIG. 5, between the free end 48 of the needle in the extraction position and the lower end of the push element 60.

The incline angle A1, visible in FIG. 5, between the first face 76 and the direction Y-Y' of movement of the push element is between 10° and 35°, preferably equal to 14°.

The cam surface 64 being situated on the push element 60, the push element 60 forms the synchronization means 35 between the extraction means 32 and the generating means 34 to generate an over-pressure in the conduit 30 during removal of the needle 28.

The height Hc of the chamber 14 is substantially equal to the travel of the free end 48 of the needle in the reservoir 18 and the septum 20 intended to rise slightly during the removal of the needle 28, such that the synchronization means 35 is capable of activating the generating means 34 substantially only when the free end 48 of the needle is situated in the chamber 14, during the extraction phase of the needle.

In the described embodiment, the length Lp1 of the orthogonal projection of the first face 76 is substantially equal to the height Hc of the chamber 14, such that the synchronization means 35 is capable of activating the generating means 34 substantially during the entire duration of the extraction phase of the needle, during which the free end 48 of the needle is situated in the chamber 14.

Figure 4:
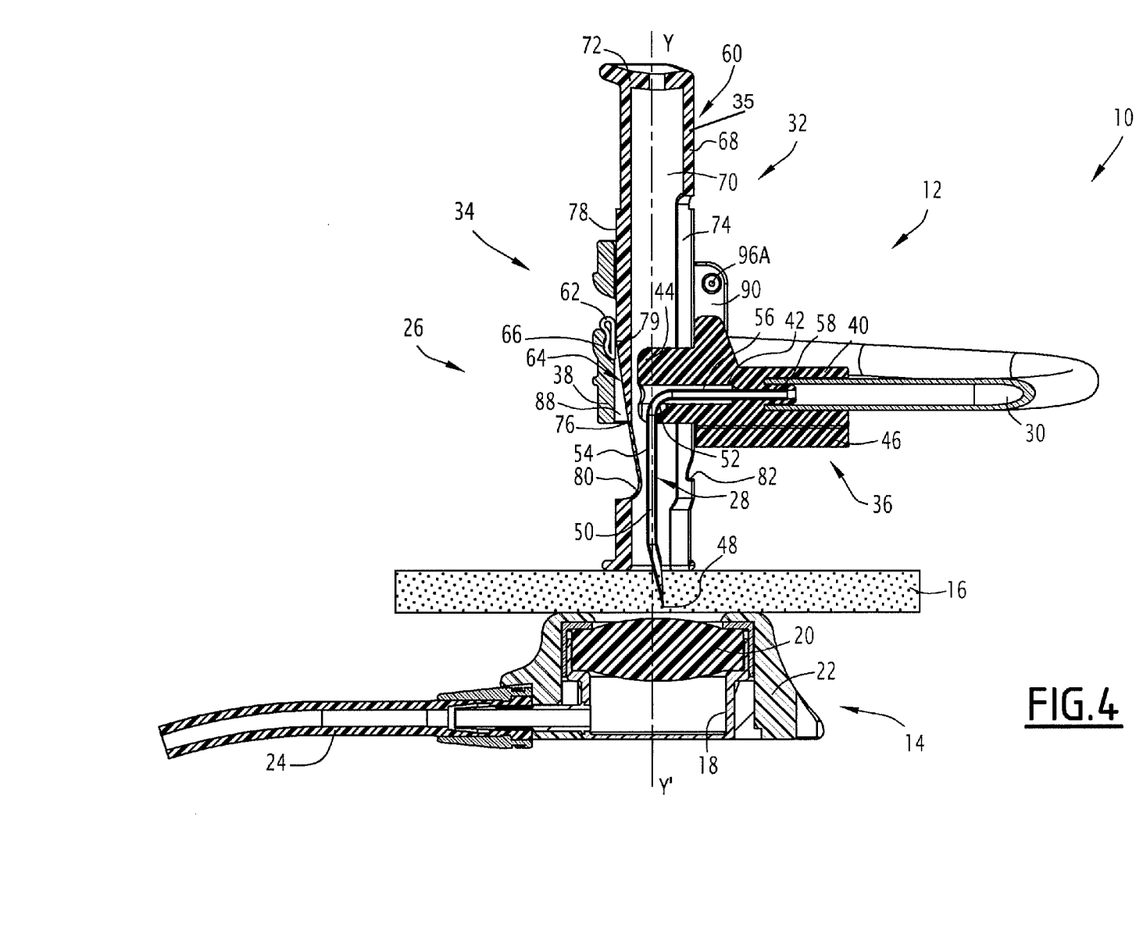
FIG. 4 is a view similar to that of FIG. 3, the needle being substantially halfway through its removal travel from the use position to the extraction position.

In FIG. 4, the faces 76, 78 are disposed on the side of the rod 68, which is opposite the slot 74. The rod 68 has, at the front end of the first face 76, a groove 80 for receiving a flexible segment 62 in the inactive position of the extraction means 32.

The rod 68 includes, near the groove 80, an outer annular slot 82 intended to receive elastic triggering elements 84, visible in FIG. 2 and integral with the sleeve 38. The slot 82 and the elements 84 are capable of ensuring temporary retention of the push element 60 in the inactive position of the extraction means 32.

The injection device 10 also includes retaining means 86 of the flexible segment 62. In the described embodiment, the retaining means 86 is capable of maintaining the flexible segment 62 substantially perpendicular to the plane of the needle 28.

The sleeve 38 defines a passage 88 for circulation of the push element 60. The sleeve 38 is laterally open following a generatrix over a width corresponding to the width of the central core 40 of the holder.

On either side of said opening, the sleeve 38 is extended by two flanks 90 capable of engaging around the central core 40. For the articulation of the sleeve 38 on the central core 40, the flanks 90 are pierced with two circular holes, in which studs 92 are received, visible in FIG. 2, integral with the central core 40 and extending along the hinge pin X-X'. The hinge pin is placed near the head 44, such that in the extraction position of the needle 28 or tilted position of the sleeve 38, the head 44 extends inside the passage 88.

At its end opposite the head 44, the sleeve 38 outwardly has two radial protuberances 94 forming a bearing-finger, as shown in FIG. 2.

The sleeve 38 has, on its flanks 90, protruding profiles 96A, visible in FIG. 3, for elastic triggering in the complementary hollow profiles 96B of the core 40, visible in FIG. 2, to ensure temporary immobilization of the extraction means 32 in a folded position of the sleeve 38 on the holder 36 as illustrated by FIG. 1.

In FIG. 1, the flexible segment 62 extends between, upstream, an end 98 for connecting to a reservoir, not shown, of liquid to be injected, and downstream, the stud 58.

The injection device 12 comprises additional means 100 for covering the injection conduit 30, disposed upstream of the means 34 for generating the over-pressure. The additional covering means 100 is formed by a clip 100 able to effectively cover the injection conduit 30 upstream of the device 12 and disposed on the flexible segment 62 between the reservoir, not shown, and the core 40.

The retaining means 86 includes a channel 102 for receiving the flexible segment 62, formed in the sleeve 38, as shown in FIG. 2. In the described embodiment, the channel 102 extends substantially perpendicular to the needle 28, in the direction of axis X-X'. The channel 102 includes two openings 104 for passage of the flexible segment and an insertion opening 106 of the flexible segment, visible in FIG. 2. The passage openings 104 have normals substantially along the direction of axis X-X' and the insertion opening 106 is substantially perpendicular to the passage openings 104. The openings 104, 106 communicate with corresponding outer faces of the sleeve 38.

The bearing surface 66 is a flank, visible in FIG. 2, of the receiving channel 102 disposed substantially parallel to the direction of movement of the push element 60. The insertion opening 106 is substantially parallel to the flank 66.

The groove 80 of the rod of the push element is substantially in the direction of the channel 102 formed in the sleeve 38.

The operation of the injection system 10 according to the invention will now be described.

Initially, during the product injection, the extraction means 32 is in its inactive position and folded along the length of the central core 40 of the needle holder, as shown in FIG. 1. To inject the drug dose, the needle 28 is engaged through the patient's skin 16 in the chamber 14 until the plate 46 bears on the patient's skin 16.

The folded extraction means 32 is then not bothersome for manipulation. Moreover, the push element 60 being folded down along the central core 40, the latter does not protrude along its entire length relative to the patient's skin 16, such that the injection device 12, after placement, can easily be maintained by an adhesive tape. The means 34 for generating an over-pressure is inactive.

To remove the injection device 12, the sleeve 38 and the push element 60 are tilted around axis X-X' to be brought into the position illustrated in FIGS. 2 and 3. The practitioner then inserts the flexible segment 62 through the insertion opening 106 in the channel 102 of the sleeve, as shown in FIG. 2. The push element 60 is placed in the axis Y-Y' of the main segment 54 of the needle, and the two protuberances 94 generally extend perpendicular to the axis Y-Y'. The head 44 of the holder is received in the hollowed out push element 60.

Next, the practitioner covers the injection conduit 30 by activating the clip 100 situated upstream of the flexible segment 62. He then applies two fingers on either side of the sleeve 38 under the bearing-fingers 94 and pushes in the push element 60 using another finger, for example his thumb, bearing on the bearing-finger 72.

The front end of the push element 60 bears on the patient's skin 16, while the sleeve 38 is made to rise along the length of the push element 60. The needle 28 is thus gradually taken inside the push element 60 until it is brought into the position illustrated in FIG. 5. In this position and due to the securing distance Ds, the main segment 54 of the needle extends completely inside the inner volume 70 of the push element and is protected, thereby avoiding any risk of accidental pricking.

When the needle 28 is removed, the cam surface 64 moves towards the flexible segment 62 and perpendicular thereto. The movement of the cam surface 64 occurs in two successive steps.

During the first step, the flexible segment 62 is gradually compressed between the first face 76 and the bearing surface 66, generating an over-pressure from upstream to downstream in the conduit 30 due to the incline of the first face 76 relative to the bearing surface 66 and due to the covering of the conduit 30 upstream of the flexible segment 62 by the clip 100. This first step is completed when the flexible segment 62 is in contact with the connecting edge 79, as shown in FIG. 4. At the end of this first step, the portion of the flexible segment 62 disposed in the channel 102 is completely pinched between the flank 66 and the cam surface 64.

The generation of the over-pressure from upstream to downstream in the injection conduit 30 causes a flow of liquid from upstream to downstream. This flow prevents blood from penetrating the tube 24 connected to the chamber 14 during extraction of the needle 28.

The maximum value of the over-pressure, and consequently the injection speed of the liquid, depends on the incline angle A1 between the first face 76 and the direction Y-Y' of movement of the push element 60, the inner diameter Di of the flexible segment 62 and the length Lt of the portion of the flexible segment 62 compressed between the cam surface 64 and the bearing surface 66. For an angle A1 equal to 14°, an inner diameter Di equal to 2 mm and a length Lt equal to 10 mm, the injection speed is close to 8 μL for 2 mm of needle removal.

During the second step, the flexible segment 62 is kept compressed between the second face 78 and the bearing surface 66. The second face 78 and the bearing surface 66 being parallel, no over-pressure is generated during said second phase of the movement of the cam surface 64. This second step is completed when the push element 60 is in the extraction position of the needle 28, as shown in FIG. 5.

The entire over-pressure that could be generated in the conduit 30 during removal of the needle was generated during the first step of the movement of the cam surface 64 and from the beginning of removal of the needle 28. This first step corresponds to the duration of the extraction phase of the needle 28, during which the free end 48 of the needle is situated in the chamber 14.

The shape of the cam 64 makes it possible to adjust the liquid injection as a function of the removal of the needle.

It will be understood that only the injection of liquid when the free end 48 of the needle is still in the chamber 14 is useful to avoid suctioning blood at the catheter end.

The injection system according to the invention makes it possible to guarantee that all of the liquid contained in the portion of the flexible segment 62 intended to be compressed is injected when the free end 48 of the needle is still in the chamber 14, the synchronization means 35 being capable of activating the generating means 34 substantially only when the free end 48 of the needle is situated in the chamber 14, during the extraction phase of the needle 28.

The generation of the over-pressure is thus improved by only being done during the entire duration of the extraction phase of the needle, during which the free end of the needle is situated in the chamber. The volume of liquid injected in the hose 24 connected to the chamber 14 is maximized for the portion of the flexible segment 62 intended to be compressed, in order to prevent an obstruction of the catheter by greatly reducing, or even eliminating the residual volume of blood at the catheter end.

The volume useful to inject liquid is minimal and the injection system according to the invention does not require dead volume, which is a source of complications due to its difficulty in being rinsed and bled.

According to another embodiment, the retaining means 86 is capable of maintaining the flexible segment 62 substantially in the direction of the main segment 54 of the needle. The compression of the flexible segment 62 is axial and in the direction of the main segment 54 of the needle. The channel 102 for receiving the flexible segment formed in the sleeve extends substantially in the direction of the main segment 54 of the needle, in the direction of axis Y-Y'.

The invention claimed is:

1. A system for injecting liquid into a body, such as that of a patient, the system comprising:
    an implantable chamber capable of being disposed under the patient's skin and extended by a catheter capable of traveling in a blood vessel to an organ, where the liquid must be injected, and
    an injection device including:
        a base bearing an injection needle, the needle having a pointed free end, intended to be inserted into the body and engaged in the implantable chamber,
        an injection conduit connected to the needle,
        extraction means for extracting the needle from the patient, including a push element mounted such that it can slide in relation to the base between a needle use position and a needle extraction position,
        activatable generating means for generating excess pressure in the injection conduit, normally inactive,
        synchronizing means for synchronization between the extraction means and the generating means to activate the generating means during an extraction phase of the needle,
    wherein the synchronization means actuate the generating means along a travel of the needle that is substantially less than or equal to the height of the implantable chamber, so that the generating means are actuated substantially only when the free end of the needle is located in the implantable chamber, during the needle extraction phase.

2. The system according to claim 1, characterized in that the synchronization means is capable of actuating the generating means substantially during the entire duration of the needle extraction phase, during which the free end of the needle is situated in the implantable chamber.

3. The system according to claim 1, characterized in that said generating means comprises a flexible segment formed in the injection conduit, a cam surface integral with the push element, and a bearing surface integral with the base, to compress said flexible segment between the cam surface and the bearing surface, during sliding of the push element towards the extraction position of the needle.

4. The system according to claim 3, characterized in that the cam surface is formed by two distinct and adjacent faces of the push element, the first face being inclined relative to the direction of movement of the push element and oriented towards the bearing surface, and the second face being substantially parallel to the direction of movement of the push element.

5. The system according to claim 4, characterized in that the length of the second face in the direction of movement of the push element is greater than or equal to the sum of 3 mm and a securing distance between the free end of the needle in the extraction position and the lower end of the push element, the sliding of the push element towards the extraction position of the needle taking place from top to bottom.

6. The system according to claim 4, wherein the incline angle between the first face and the direction of movement of the push element is between 10° and 35°.

7. The system according to claim 4, wherein the incline angle between the first face and the direction of movement of the push element is equal to 14°.

8. The system according to claim 1, characterized in that the injection device comprises additional means for covering the injection conduit, arranged upstream of the means for generating the over-pressure.

9. The system according to claim 1, characterized in that the base includes a needle holder and a sleeve, said sleeve being hinged relative to the needle holder and defining a sliding passage of the push element.

10. A system for injecting liquid into a body, such as that of a patient, the system comprising:
- an implantable chamber capable of being disposed under the patient's skin and extended by a catheter capable of traveling in a blood vessel to an organ, where the liquid is to be injected, and
- an injection device including:
  - a base bearing an injection needle, the needle having a pointed free end, intended to be inserted into the body and engaged in the implantable chamber,
  - an injection conduit connected to the needle,
  - extraction means for extracting the needle from the patient, including a push element mounted such that it can slide in relation to the base between a needle use position and a needle extraction position,
  - activatable generating means for generating excess pressure in the injection conduit, which is normally inactive,
  - synchronizing means for synchronization between the extraction means and the generating means to activate the generating means during an extraction phase of the needle, wherein:
- the synchronization means is configured to actuate the generating means substantially only when the free end of the needle is located in the implantable chamber, during the needle extraction phase,
- said generating means comprises a flexible segment formed in the injection conduit, a cam surface integral with the push element, and a bearing surface integral with the base, to compress said flexible segment between the cam surface and the bearing surface, during sliding of the push element towards the extraction position of the needle,
- the cam surface is formed by two distinct and adjacent faces of the push element, the first face being inclined relative to the direction of movement of the push element and oriented towards the bearing surface, and the second face being substantially parallel to the direction of movement of the push element, and
- the length of the orthogonal projection of the first face over the direction of movement of the push element is substantially less than or equal to the height of the implantable chamber in the direction of movement of the push element.

11. A system for injecting liquid into a body, such as that of a patient, the system comprising:
- an implantable chamber capable of being disposed under the patient's skin and extended by a catheter capable of traveling in a blood vessel to an organ, where the liquid is to be injected, and
- an injection device including:
  - a base bearing an injection needle, the needle having a pointed free end, intended to be inserted into the body and engaged in the implantable chamber,
  - an injection conduit connected to the needle,
  - extraction means for extracting the needle from the patient, including a push element mounted such that it can slide in relation to the base between a needle use position and a needle extraction position,
  - activatable generating means for generating excess pressure in the injection conduit, normally inactive,
  - synchronizing means for synchronization between the extraction means and the generating means to activate the generating means during an extraction phase of the needle, wherein:
- the synchronization means can actuate the generating means substantially only when the free end of the needle is located in the implantable chamber, during the needle extraction phase,
- said generating means comprises a flexible segment formed in the injection conduit, a cam surface integral with the push element, and a bearing surface integral with the base, to compress said flexible segment between the cam surface and the bearing surface, during sliding of the push element towards the extraction position of the needle,
- the cam surface can be moved substantially perpendicular to the flexible segment during extraction of the needle.

* * * * *